US009340490B2

(12) United States Patent
Okura et al.

(10) Patent No.: US 9,340,490 B2
(45) Date of Patent: May 17, 2016

(54) DIAGNOSTIC AGENT FOR TUMOR

(75) Inventors: Ichiro Okura, Yokohama (JP); Toshiaki Kamachi, Yokohama (JP); Shunichiro Ogura, Yokohama (JP); Masahiro Ishizuka, Minato-ku (JP); Tohru Tanaka, Minato-ku (JP)

(73) Assignee: SBI PHARMACEUTICALS CO., LTD., Tokyo (JP)

( * ) Notice: Subject to any disclaimer, the term of this patent is extended or adjusted under 35 U.S.C. 154(b) by 644 days.

(21) Appl. No.: 11/664,065

(22) PCT Filed: Sep. 22, 2005

(86) PCT No.: PCT/JP2005/017520
§ 371 (c)(1),
(2), (4) Date: Apr. 25, 2007

(87) PCT Pub. No.: WO2006/035678
PCT Pub. Date: Apr. 6, 2006

(65) Prior Publication Data
US 2008/0108701 A1 May 8, 2008

(30) Foreign Application Priority Data

Sep. 29, 2004 (JP) .............................. P. 2004-284078
Aug. 11, 2005 (JP) .............................. P. 2005-232996

(51) Int. Cl.
| | |
|---|---|
| A61K 31/197 | (2006.01) |
| A61P 43/00 | (2006.01) |
| C07C 229/22 | (2006.01) |
| A61K 49/00 | (2006.01) |
| G01N 33/574 | (2006.01) |

(52) U.S. Cl.
CPC ........... *C07C 229/22* (2013.01); *A61K 49/0021* (2013.01); *G01N 33/574* (2013.01)

(58) Field of Classification Search
CPC . C07C 229/22; A61K 49/0021; G01N 33/574
USPC ...................... 424/9.6, 59; 560/170; 564/198; 514/551, 626
See application file for complete search history.

(56) References Cited

U.S. PATENT DOCUMENTS

| | | | | |
|---|---|---|---|---|
| 4,372,974 | A | * | 2/1983 | Fish et al. ....................... 514/561 |
| 6,492,420 | B2 | * | 12/2002 | Gierskcky et al. ............. 514/551 |
| 6,905,671 | B1 | * | 6/2005 | Tanaka et al. ................... 424/9.6 |
| 7,289,205 | B2 | * | 10/2007 | Yaroslavsky et al. ......... 356/317 |

FOREIGN PATENT DOCUMENTS

| | | |
|---|---|---|
| CA | 2 215 069 C | 9/2006 |
| CN | 1178521 A | 4/1998 |
| JP | 4-9360 A | 1/1992 |
| JP | 11-12197 A | 1/1999 |
| JP | 11-501914 A | 2/1999 |

OTHER PUBLICATIONS

Hua et al, Cancer Research, 55, 1723-1731, 1995.*
Wolff, M.E. "Burger's Medicinal Chemistry 4th Ed. Part I", Wiley: New York, 1979, 336-337.*
Wolff, Manfred E. "Burger's Medicinal Chemistry, 5ed, Part I", John Wiley & Sons, 1995, pp. 975-977.*
Banker (Modern Pharmaceutics) Banker, G.S. et al, "Modern Pharmaceutics, 3ed.", Marcel Dekker, New York, 1996, pp. 451 and 596.*
West, Anthony R., Solid State Chemistry and its Applications, Wiley, New York, 1988, pp. 358 & 365. Bernard Testa "Predicting drug metabolism: Concepts and challenges" Pure and Applied Chemistry 2004, vol. 76, No. 5, pp. 907-914.*
Lippert B.M., Excretion Measurement of Porphyrins and Their Precursors After Topical Administration of 5-Aminolaevulinic Acid for Fluorescence Endoscopy in Head and Neck Cancer, Research Communications in Molecular Pathology and Pharmacology, 2003, vol. 113, 114, pp. 75 to 85.
Casas A., Tissue distribution and kinetics of endogenous porphyrins synthesized after topical application of ALA in different vehicles, British Journal of Cancer, 1999, vol. 81, No. 1, pp. 13-18.
Egger N.G. et al., Accumulatino of Porphyrins in Plasma and Tissues of Dogs after Aminolevulinic Acid Administration: Implications for Photodynamic Therapy, Pharmacology, 1996, vol. 52, No. 6, pp. 362-370.
Office Action mailed Apr. 10, 2009 in Chinese Application No. 2005800329840.
Chinese Office Action dated Nov. 6, 2009, corresponding to Chinese Application No. 2005800329840.
Australian Office Action dated Feb. 2, 2010 in Australian Application No. 2005288361.
Japanese Office Action issued in Application No. 2005-232996, dated Dec. 21, 2010.
Norio Mitsuyoshi, et al.; "Fluorescence analysis of protoporphyrin-IX (Pp-IX) which is a metabolite in tumor upon administration of 5-aminolevulinic acid (5-ALA)"; Nippon Laser Igaku Kaishi, Sep. 2002, vol. 23 No. 3; pp. 81-88.

(Continued)

*Primary Examiner* — Shailendra Kumar
(74) *Attorney, Agent, or Firm* — Sughrue Mion, PLLC

(57) ABSTRACT

According to the present invention, a tumor diagnostic agent which carries out early stage detection, monitoring of therapeutic effect and prognostic diagnosis of all tumors The tumor diagnostic agent of the present invention is a tumor diagnostic agent comprising δ-aminolevulinic acid represented by formula (I), a derivative thereof and a salt thereof:

$$R^2R^1NCH_2COCH_2CH_2COR^3 \qquad (I)$$

wherein $R^1$ and $R^2$ each independently represents hydrogen, alkyl, acyl, alkoxycarbonyl, aryl or aralkyl; and $R^3$ represents hydroxy, alkoxy, acyloxy, alkoxycarbonyloxy, aryloxy, aralkyloxy or amino, which is used for diagnoses by measuring porphyrins in a sample collected from the inside or outside of the body after its administration.

5 Claims, 2 Drawing Sheets

(56) References Cited

OTHER PUBLICATIONS

Yasuhiro Mizokami, et al.; "Measurement of porphyrin in plasma of cancer-bearing mice"; Accumulated Papers to be Presented at the Japan Chemical Society; Mar. 11, 2004; vol. 84 No. 2; p. 1121.

Japanese Office Action issued on Mar. 15, 2011 in the corresponding Japanese Patent Application No. 2005-232996.

Udagawa, M. et., al. "Aberrant Porphyrin Metabolism in Hepatocellular Carcinoma", Biomedical Medicine, Apr. 1984, vol. 31, pp. 131-139.

Canadian Office Action issued Nov. 21, 2011 in corresponding Canadian Patent Application No. 2,581,204.

Extended European Search Report issued on Jun. 7, 2011 in the corresponding European Patent Application No. 05785787.2.

Manivasager, V. et al., "A Study of 5-aminolevulinic acid and its methyl ester used in in vitro and in vivo systems of human bladder cancer", International Journal of Oncology, vol. 22, 2003, pp. 313-318.

Communication dated Jan. 17, 2012, issued by the Japanese Patent Office in corresponding Japanese Patent Application No. 2005-232996.

Office Action issued Aug. 6, 2013, by the Japanese Patent Office in corresponding Japanese Application No. 2012-054612.

European Office Action dated Oct. 10, 2012 issued by the European Patent Office in corresponding European Patent Application No. 05785787.2.

Communication, dated Apr. 2, 2015, issued by the European Patent Office in counterpart European Patent Application No. 05785787.2.

Duska et al., "Detection of Female Lower Genital Tract Dysplasia Using Orally Administered 5-Aminolevulinic Acid Induced Protoporphyrin IX: A Preliminary Study", Gynecologic Oncology, vol. 85, No. a, Apr. 1, 2002, pp. 125-128.

Canadian Office Action, dated Nov. 4, 2010, issued in Application No. 2,581,204.

* cited by examiner

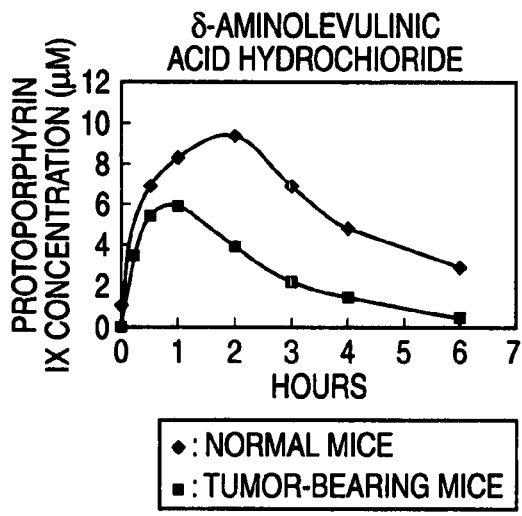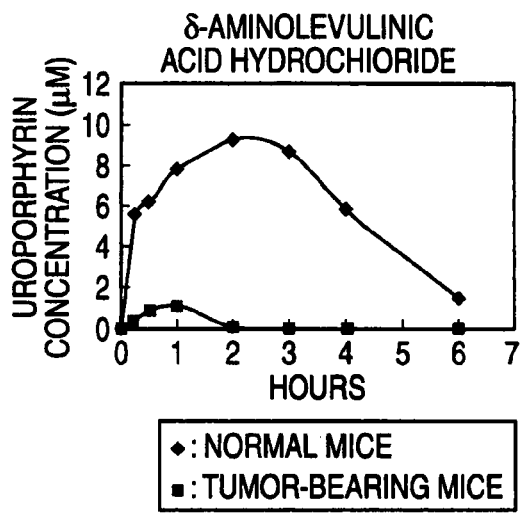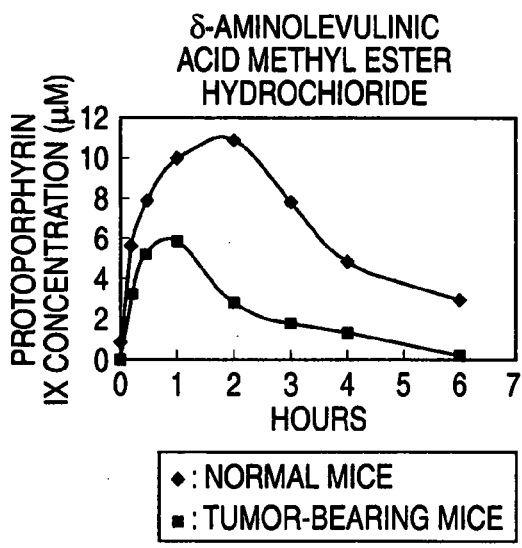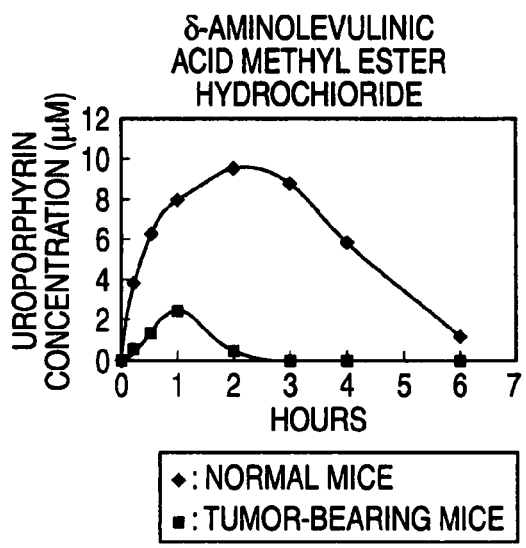

DIAGNOSTIC AGENT FOR TUMOR

This application is a 371 of PCT/JP05/17520, filed on Sep. 22, 2005.

TECHNICAL FIELD

The present invention relates to a novel tumor diagnostic agent which comprises δ-aminolevulinic acid, a derivative thereof or a salt thereof.

BACKGROUND ART

Early stage detection is the most important matter for treating tumors. Conventionally, each tumor has been detected by measuring respective substance in blood, generally called a tumor marker. The tumor marker is defined as "among substances which produce cancer cells or substances which are produced by normal cells in the body by reacting with cancer cells, those in which their inspection by blood, tissues, excrements (urine and feces) and the like serves as a marker for the diagnosis or treatment of cancers".

However, since most of the tumor markers are also produced in small amounts caused by diseases other than cancers, they sometimes show false positive in the case of chronic inflammation and the like. For example, it is said that since carcinoembryonic antigen (CEA) is produced by the cells of many organs such as the stomach, large intestine, pancreas, lungs and the like, it causes about 20% of false positive. In addition, since there are tumors whose appropriate tumor markers have not been found, it is the current situation that a tumor marker which can cover all tumors is not present.

On the other hand, it is known that when δ-aminolevulinic acid (ALA) or a derivative thereof is administered, the protoporphyrin IX induced is accumulated into the tumor and exerts its effect for intraoperative diagnosis and treatment (Patent References 1 and 2).

Patent Reference 1: JP-A-11-12197
Patent Reference 2: JP-T-11-501914

DISCLOSURE OF THE INVENTION

Problems to be Solved by the Invention

However, according to the above-described methods, it is necessary to prepare an isotope of δ-aminolevulinic acid (Patent Reference 1), and it is necessary to mix a collected body fluid (cells contained in the body fluid) with an ALA ester and to expose the mixture to light (Patent Reference 2).

In addition, analysis of porphyrin in the blood samples of cancer patients has been attempted, but has not been resulted yet in the diagnosis of the cancer because of the low porphyrin concentration.

Accordingly, an object of the invention is to provide a tumor diagnostic agent which carries out early stage detection, monitoring of therapeutic effect and prognostic diagnosis of all tumors, by analyzing porphyrins in the samples collected from the inside or outside of the body, typified by blood and urine after administration of ALA.

Means for Solving the Problems

By taking such present situation into consideration, the present inventors have conducted intensive studies on a novel tumor diagnostic agent which can cover all tumors and found as result that tumors can be detected with high sensitivity when δ-aminolevulinic acid, a derivative thereof or a salt thereof is administered and then porphyrins in the samples collected from the inside or outside of the body are measured, thereby resulting in the accomplishment of the present invention.

That is, the present invention relates to the following (1) to (11).

(1) A compound selected from δ-aminolevulinic acid represented by formula (I), a derivative thereof and a salt thereof, which is used for a tumor diagnostic agent for diagnoses by measuring porphyrins in a sample collected from the inside or outside of the body after its administration:

$$R^2R^1NCH_2COCH_2CH_2COR^3 \qquad (I)$$

wherein $R^1$ and $R^2$ each independently represents hydrogen, alkyl, acyl, alkoxycarbonyl, aryl or aralkyl; and $R^3$ represents hydroxy, alkoxy, acyloxy, alkoxycarbonyloxy, aryloxy, aralkyloxy or amino.

(2) Use of δ-aminolevulinic acid represented by formula (I), a derivative thereof or a salt thereof as a tumor diagnostic agent for diagnoses by measuring porphyrins in a sample collected from the inside or outside of the body after its administration:

$$R^2R^1NCH_2COCH_2CH_2COR^3 \qquad (I)$$

wherein $R^1$ and $R^2$ each independently represents hydrogen, alkyl, acyl, alkoxycarbonyl, aryl or aralkyl; and $R^3$ represents hydroxy, alkoxy, acyloxy, alkoxycarbonyloxy, aryloxy, aralkyloxy or amino.

(3) Use of δ-aminolevulinic acid represented by formula (I), a derivative thereof or a salt thereof for the manufacture of a tumor diagnostic agent for diagnoses by measuring porphyrins in a sample collected from the inside or outside of the body after its administration:

$$R^2R^1NCH_2COCH_2CH_2COR^3 \qquad (I)$$

wherein $R^1$ and $R^2$ each independently represents hydrogen, alkyl, acyl, alkoxycarbonyl, aryl or aralkyl; and $R^3$ represents hydroxy, alkoxy, acyloxy, alkoxycarbonyloxy, aryloxy, aralkyloxy or amino.

(4) The compound or use according to any one of (1) to (3), wherein the tumor tissue is brain, nasal tract, nasal cavity, trachea, bronchus, oral cavity, pharynx, esophagus, stomach, breast, colorectum, lung, ovary, central nervous system, liver, bladder, urethra, ureter, pancreas, cervical duct, abdominal cavity, anal canal or cervix uteri.

(5) The compound or use according to any one of (1) to (4), wherein the porphyrins are protoporphyrin IX, uroporphyrin I, uroporphyrin III, coproporphyrin I, coproporphyrin III, heptacarboxylporphyrin I, heptacarboxylporphyrin III, hexacarboxylporphyrin I, hexacarboxylporphyrin III, pentacarboxylporphyrin I, pentacarboxylporphyrin III, isocoporphyrin, harderoporphyrin, isoharderoporphyrin, mesoporphyrin IX, deuteroporphyrin IX or pemptoporphyrin.

(6) The compound or use according to any one of (1) to (5), wherein the δ-aminolevulinic acid, derivative thereof or salt thereof is administered at a dose of from 0.001 mg to 10 g per 1 kg body weight per once.

(7) The compound or use according to any one of (1) to (6), which is used for oral administration, intraperitoneal administration, intravenous administration, intramuscular administration, affected part topical application, percutaneous absorption or rectal administration.

(8) The compound or use according to any one of (1) to (7), wherein the sample collected from the inside or outside of the body is blood, body fluid, tissue, urine, feces, saliva, sweat, cerebrospinal fluid, semen or tears.

(9) The compound or use according to any one of (1) to (8), wherein the sample is collected from the inside or outside of the body after from 0.1 to 10 hours of the administration of the δ-aminolevulinic acid, derivative thereof or salt thereof.
(10) The compound or use according to any one of (1) to (9), wherein uroporphyrin I and uroporphyrin III are measured, and a tumor is detected based on the uroporphyrin I/uroporphyrin III concentration ratio.
(11) The compound or use according to any one of (1) to (10), wherein the porphyrins are measured using BPLC (high performance liquid chromatography), TLC (thin layer chromatography), fluorescence detection or immunoassay.

Effect of the Invention

According to the tumor diagnostic agent of the present invention, early stage detection, monitoring of therapeutic effect and prognostic diagnosis of tumors can be carried out conveniently without limitation to a specific tumor.

BEST MODE FOR CARRYING OUT THE INVENTION

Figures 1, 2, 3, 4, 5:
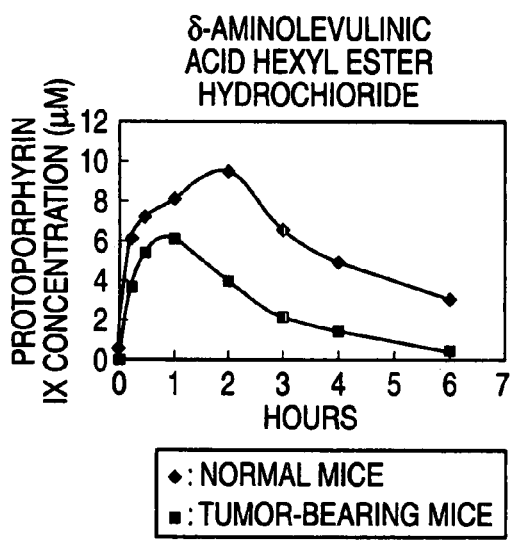
FIG. 1 is a graph showing changes in the concentration of protoporphyrin IX and uroporphyrin in tumor-bearing mice and normal mice by a fluorescence detection method.

Conventionally, attempts have not been made to administer δ-aminolevulinic acid, a derivative thereof or a salt thereof, collect samples from the inside or outside of the body and then measure porphyrins in the samples. The tumor diagnostic agent of the present invention is a diagnostic agent for detecting tumors, by administering δ-aminolevulinic acid, a derivative thereof or a salt thereof and then measuring porphyrins in a sample collected from the inside or outside of the body.

Active ingredient of the tumor diagnostic agent of the present invention is δ-aminolevulinic acid, a derivative thereof (the above-described formula (I)) or a salt thereof.

In formula (I), the alkyl represented by $R^1$ or $R^2$ is preferably linear or branched alkyl having from 1 to 24 carbon atoms, more preferably alkyl having from 1 to 18 carbon atoms, and most preferably alkyl having from 1 to 6 carbon atoms. The alkyl having from 1 to 6 carbon atoms includes methyl, ethyl, n-propyl, isopropyl, n-butyl, sec-butyl and the like. The acyl is preferably linear or branched alkanoyl, alkenylcarbonyl or aroyl having from 1 to 12 carbon atoms, and more preferably alkanoyl having from 1 to 6 carbon atoms. The acyl includes formyl, acetyl, propionyl, butyryl and the like. The alkoxycarbonyl is preferably alkoxycarbonyl having from 2 to 13 total carbon atoms, and more preferably alkoxycarbonyl having from 2 to 7 carbon atoms. The alkoxycarbonyl includes methoxycarbonyl, ethoxycarbonyl, n-propoxycarbonyl, isopropoxycarbonyl and the like. The aryl is preferably aryl having from 6 to 16 carbon atoms, such as phenyl and naphthyl. The aralkyl is preferably a group composed of the aryl having from 6 to 16 carbon atoms and the above-described alkyl having from 1 to 6 carbon atoms, such as benzyl.

The alkoxy represented by $R^3$ is preferably linear or branched alkoxy having from 1 to 24 carbon atoms, more preferably alkoxy having from 1 to 16 carbon atoms, and most preferably an alkoxy having from 1 to 12 carbon atoms. The alkoxy includes methoxy, ethoxy, n-propoxy, isopropoxy, n-butoxy, pentyloxy, hexyloxy, octyloxy, decyloxy, dodecyloxy and the like. The acyloxy is preferably linear or branched alkanoyloxy having from 1 to 12 carbon atoms, and more preferably alkanoyloxy having from 1 to 6 carbon atoms. The alkanoyloxy includes acetoxy, propionyloxy, butyryloxy and the like. The alkoxycarbonyloxy is preferably alkoxycarbonyloxy having from 2 to 13 total carbon atoms, and more preferably alkoxycarbonyloxy having from 2 to 7 total carbon atoms. The alkoxycarbonyloxy includes methoxycarbonyloxy, ethoxycarbonyloxy, n-propoxycarbonyloxy, isopropoxycarbonyloxy and the like. The aryloxy is preferably aryloxy having from 6 to 16 carbon atoms, such as phenoxy and naphthyloxy. The aralkyloxy is preferably a group having the above-described aralkyl, such as benzyloxy.

In formula (I), $R^1$ and $R^2$ each is preferably hydrogen. $R^3$ is preferably hydroxy, alkoxy or aralkyloxy, more preferably hydroxy or alkoxy having from 1 to 12 carbon atoms, and most preferably methoxy or hexyloxy.

The δ-aminolevulinic acid derivative includes δ-aminolevulinic acid methyl ester, δ-aminolevulinic acid ethyl ester, δ-aminolevulinic acid propyl ester, δ-aminolevulinic acid butyl ester, δ-aminolevulinic acid pentyl ester, δ-aminolevulinic acid hexyl ester and the like, and δ-aminolevulinic acid methyl ester or δ-aminolevulinic acid hexyl ester is particularly preferable.

As the salt of δ-aminolevulinic acid or a derivative thereof, a pharmacologically acceptable acid addition salt of an inorganic acid or organic acid is preferable, although not particularly limited. The inorganic acid addition salt includes hydrochloride, hydrobromide, sulfate, nitrate, phosphate and the like, and the organic acid addition salt includes acetate, lactate, citrate, tartarate, succinate, maleate, fumarate, ascorbate and the like, and δ-aminolevulinic acid hydrochloride or δ-aminolevulinic acid phosphate is preferred.

These salts can be produced by any one of the methods which use chemical syntheses, microorganisms or enzymes. Examples include the methods described in JP-A-4-9360, JP-T-11-501914, Japanese Patent Application Nos. 2004-99670, 2004-99671 and 2004-99672.

The tumor diagnostic agent of the present invention can be prepared in the usual way by mixing δ-aminolevulinic acid, a derivative thereof or a salt thereof with a pharmaceutically acceptable carrier. The dosage forms include oral administration preparations such as granules, fine subtilaes and tablets; injections such as solutions and powders for dissolution when used; percutaneous preparations such as ointments, solutions, creams and gels; suppositories and the like.

The tumors to which the tumor diagnostic agent of the present invention can be applied are malignant or non-malignant tumors. The malignant tumors proliferate in an infiltrating manner and show a malignancy such as metastasis. Among the malignant tumors, tumors derived from epithelial cells occupy most part thereof, and sarcoma, lymphomatosis and leukemia are also included therein. The non-malignant tumors show diseases other than the malignant tumors, such as benign diseases, and do not always mean that their treatment is easy.

Although the tumor tissue is not particularly limited, it includes brain, nasal tract, nasal cavity, trachea, bronchus, oral cavity, pharynx, esophagus, stomach, breast, colorectum, lung, ovary, central nervous system, liver, bladder, urethra, ureter, pancreas, cervical duct, abdominal cavity, anal canal, cervix uteri and the like.

The administration method of the tumor diagnostic agent of the present invention includes oral administration, intravenous administration, intramuscular administration, affected part topical application, intraperitoneal administration, percutaneous absorption, rectal administration and the like, and intraperitoneal administration, oral administration, affected part topical application or intravenous administration is preferable.

Dose of the tumor diagnostic agent of the present invention varies depending on the administration method, route of administration, symptom, body weight and kind of the tumor, but in the case of oral administration, it is from 0.001 to 10 g per 1 kg body weight per once, preferably from 0.1 to 1000 mg, and more preferably from 1 to 100 mg.

Regarding the sample to be collected from the inside or outside of the body after administration of the tumor diagnostic agent of the present invention, examples include blood, body fluid, tissue, urine, feces, saliva, sweat, cerebrospinal fluid, semen, tears and the like, although not particularly limited thereto. As the sample, blood, urine or feces is preferable in view of the convenience of sample collection. The period of time after the administration until the collection of the sample from the inside or outside of the body varies depending on the administration method and tumor tissue, but is from about 0.1 to 10 hours during which the existing amount of porphyrins becomes maximum, particularly from about 0.5 to 5 hours. In this connection, it is desirable that the collected samples are treated in the usual way before the subsequent measurement.

Although the porphyrins to be measured are not particularly limited, examples include protoporphyrin IX, uroporphyrin I, uroporphyrin III, heptacarboxylporphyrin I, heptacarboxylporphyrin III, hexacarboxylporphyrin I, hexacarboxylporphyrin III, pentacarboxylporphyrin I, pentacarboxylporphyrin III, coproporphyrin I, coproporphyrin III, isocoporphyrin, harderoporphyrin, isoharderoporphyrin, mesoporphyrin IX, deuteroporphyrin IX, pemptoporphyrin and the like, and protoporphyrin IX, uroporphyrin I, uroporphyrin III, coproporphyrin I or coproporphyrin III is preferable.

The above-described porphyrins can be measured by a detection method such as HPLC (high performance liquid chromatography), TLC (thin layer chromatography) or fluorescence detector, or a biological detection method such as immunoassay. The detection methods are not particularly limited, so long as determination of porphyrins can be effected, and can be optionally selected depending on the object and convenience. Among these, HPLC and TLC are suitable for detailed diagnosis because of their ability to determine respective porphyrins individually. In the case of HPLC, peaks of two or more porphyrin species may be overlapped depending on the column and liquid flow conditions, but it is possible to judge only the presence or absence of a tumor. Although the fluorescence detector can determine a certain porphyrin when a proper wavelength is selected, the fluorescence-generating wavelengths of respective porphyrins are close to one another, so that this is not suitable for the accurate determination of individual porphyrin. As is shown later in Examples, the fluorescence detector is suitable for the determination as porphyrins. The immunoassay can measure a specified porphyrin and also can measure porphyrins as the total amount.

As is shown later in Examples, the porphyrin concentration in samples was high in mice to which tumor-bearing cells were administered (tumor-bearing mice) in comparison with normal mice, thus revealing that the tumor tissue can be clearly distinguished from the normal tissue according to the tumor diagnostic agent of the present invention. In addition, since there is a significant difference between tumor-bearing mice and normal mice regarding the existing ratio of certain porphyrin species such as uroporphyrin I and uroporphyrin III (uroporphyrin I/uroporphyrin III), it was found based on this difference that tumors can be detected by the tumor diagnostic agent of the present invention using the existing ratio of certain porphyrin species as the index.

The principle of diagnosis using the tumor diagnostic agent of the present invention is based on the accumulation of porphyrins typified by protoporphyrin IX into tumors, as the metabolite when δ-aminolevulinic acid, a derivative thereof or a salt thereof is administered. Regarding the reason for the occurrence of this phenomenon, studies are in progress at various institutions, and it is said that the activity of ferrochelatase which metabolize protoporphyrin IX into heme may be low in tumors, although not distinctively known so far.

EXAMPLES

The present invention is further described below in detail with reference to examples, but the present invention is not limited thereto.

Example 1

Figures 1, 2, 3, 4, 5, 6:
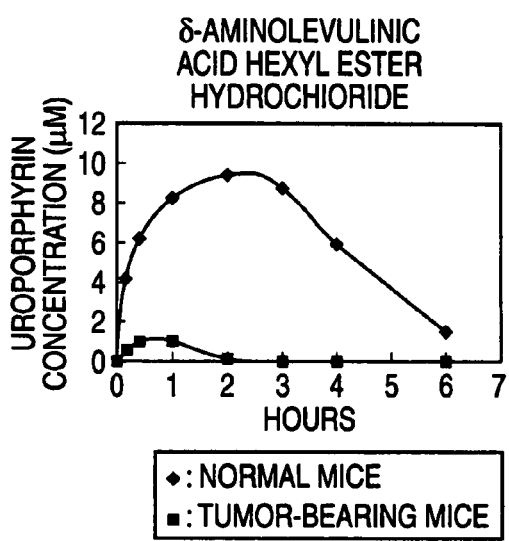
Figures 1, 2, 3, 4, 5, 6, 7:
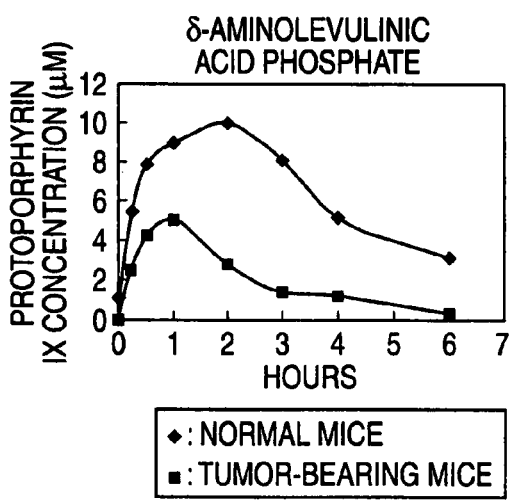
Figures 1, 2, 3, 4, 5, 6, 7, 8:
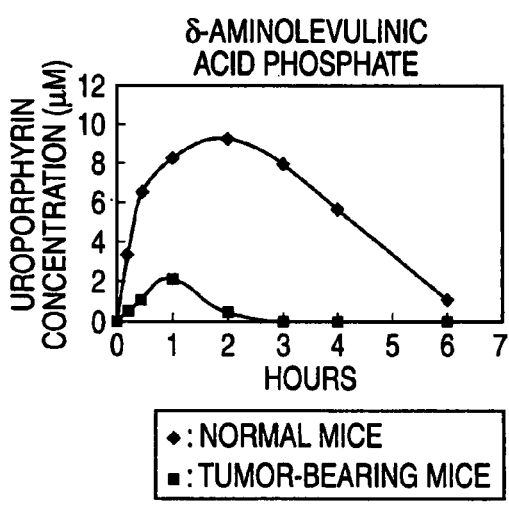

A mouse tumor-bearing cell (MH 134 cell: ascitic liver cancer cell) was intraperitoneally administered to mice (C3H/He line, 5-week-old, female) at a dose of $1\times10^6$ cells, and they were reared for 0 to 14 days. Ten days after the intraperitoneal administration of tumor-bearing cells, 50 µl of 0.12 M δ-aminolevulinic acid hydrochloride, δ-aminolevulinic acid methyl ester hydrochloride, δ-aminolevulinic acid hexyl ester hydrochloride or δ-aminolevulinic acid phosphate was orally administered to the mice to which the tumor-bearing cells had been intraperitoneally administered. From 10 to 20 µl of blood samples were collected from the orally administered mice 0, 0.25, 0.5, 2, 3, 4 or 6 hours thereafter. The thus collected blood was centrifuged at 2000×g for 5 minutes, 300 µl of ethyl acetate/acetic acid (2/1, v/v) was added to 5 µl of the supernatant (plasma), followed by mixing, 300 µl of 0.6 M NaOH solution was further added thereto, followed by mixing, and the NaOH layer was collected. To the remaining organic layer, 300 µl of 0.5 M aqueous hydrochloric acid solution was added, and the aqueous hydrochloric acid solution layer was collected. Fluorescence intensities of the NaOH layer and aqueous hydrochloric acid solution layer were measured (hydrochloric acid layer: excitation wavelength 400 nm, fluorescence wavelength 600 nm, NaOH layer: excitation wavelength 400 nm, fluorescence wavelength 619 nm), and respective concentrations were calculated from the standard solutions. In addition, δ-aminolevulinic acid hydrochloride, δ-aminolevulinic acid methyl ester hydrochloride, δ-aminolevulinic acid hexyl ester hydrochloride or δ-aminolevulinic acid phosphate was also orally administered (0.12 M, 50 µl) to normal mice as the control, and the same treatment was carried out. The results are shown in FIGS. 1-1 to 1-8.

As is apparent from FIGS. 1-1 to 1-8, concentrations of protoporphyrin IX and uroporphyrin became maximum in the mice to which the tumor-bearing cells had been intraperitoneally administered, 2 hours after the administration of δ-aminolevulinic acid hydrochloride, δ-aminolevulinic acid methyl ester hydrochloride, δ-aminolevulinic acid hexyl ester hydrochloride or δ-aminolevulinic acid phosphate. On the other hand, uroporphyrin was hardly detected in the normal mice after the 2 hours. Accordingly, it was found that the tumor diagnostic agent of the present invention is a diagnostic agent which can clearly distinguish the tumor tissue from the normal tissue.

Example 2

A mouse tumor-bearing cell (MH 134 cell) was intraperitoneally administered to mice (C3H/He line, 5-week-old, female) at a dose of 1×10⁶ cells, and they were reared for 0 to 14 days. Ten days after the intraperitoneal administration of tumor-bearing cells, 50 µl of 0.12 M δ-aminolevulinic acid hydrochloride was orally administered to the mice, and from 10 to 20 µl of blood samples were collected 2 hours thereafter. Respective blood sample was collected and then centrifuged at 2000×g for 5 minutes, 50 µl of ethyl acetate:acetic acid (2:1, v/v) was added to 5 µl of the supernatant (plasma), followed by mixing, 50 µl of 0.6 M NaOH solution was further added thereto, followed by mixing, and the NaOH layer was collected. The samples were measured by HPLC (regarding the analyzing conditions, a fluorescence detector: excitation wavelength 406 nm, fluorescence wavelength 610 nm was used, a solution consisting of 12.5% acetonitrile, 1 M ammonium acetate and 0.27 mM EDTA, pH 5.15 (adjusted with acetic acid), was used as the eluting solution, ODS-AGtypeCAPCELLPAK, 4.6 mmϕ×250 mm, particle diameter 5 µm (manufactured by Shiseido) was used as the column, and the measurement was carried out at a flow rate of 1.0 ml/min and at a temperature of 25° C.), and respective concentrations were calculated from the peak areas of standard solutions. The results are shown in Table 1.

TABLE 1

Determination of uroporphyrin I and uroporphyrin III in blood by HPLC

|  | Before administration (ng/µl) | | After administration (ng/µl) | | Ratio of uroporphyrin I/ uroporphyrin III |
|---|---|---|---|---|---|
|  | Uroporphyrin I | Uroporphyrin III | Uroporphyrin I | Uroporphyrin III |  |
| Normal mice | ND | ND | ND | ND | — |
| Tumor-bearing mice | ND | ND | 0.2 | 0.38 | 0.53 |

ND: Not Detected

As is apparent from Table 1, uroporphyrin I and uroporphyrin III were not detected in the normal mice before administration of δ-aminolevulinic acid hydrochloride, the mice to which the tumor-bearing cells were intraperitoneally administered and the normal mice after administration of δ-aminolevulinic acid hydrochloride, but in the case of the mice to which δ-aminolevulinic acid hydrochloride was administered after intraperitoneal administration of the tumor-bearing cells, uroporphyrin I and uroporphyrin III were detected, of which uroporphyrin III was frequently detected with a uroporphyrin I/uroporphyrin III ratio of 0.53. Based on this result, it was found that this is a diagnostic agent which can clearly distinguish the tumor tissue from the normal tissue based on the amounts of uroporphyrin I and uroporphyrin III and their ratio.

Example 3

A mouse tumor-bearing cell (MH 134 cell) was intraperitoneally administered to mice (C3H/He line, 5-week-old, female) at a dose of 1×10⁶ cells, and they were reared for 0 to 14 days. Ten days after the intraperitoneal administration of tumor-bearing cells, 50 µl of 0.12 M δ-aminolevulinic acid hydrochloride was orally administered to the mice, and urine samples were collected 2 hours thereafter, together with urine samples before the administration. The thus collected samples were measured by HPLC (regarding the analyzing conditions, a fluorescence detector: excitation wavelength 406 nm, fluorescence wavelength 619 nm was used, a solution consisting of 12.5% acetonitrile, 1 M ammonium acetate and 0.27 mM EDTA, pH 5.15 (adjusted with acetic acid), was used as the eluting solution, ODS-AGtypeCAPCELLPAK, 4.6 mmϕ×250 mm, particle diameter 5 µm (manufactured by Shiseido) was used as the column, and the measurement was carried out at a flow rate of 1.0 ml/min and at a temperature of 25° C.), and respective concentrations were calculated from the standard solutions. In addition, 50 µl of 0.12 M δ-aminolevulinic acid hydrochloride was also administered to the normal mice as the control, and the same treatment was carried out. The results are shown in Table 2.

TABLE 2

Determination of uroporphyrin I and uroporphyrin III in urine by HPLC

|  | Before administration (ng/µl) | | After administration (ng/µl) | | Ratio of uroporphyrin I/ uroporphyrin III |
|---|---|---|---|---|---|
|  | Uroporphyrin I | Uroporphyrin III | Uroporphyrin I | Uroporphyrin III |  |
| Normal mice | ND | ND | 0.95 | 1.01 | 0.94 |
| Tumor-bearing mice | ND | ND | 11.95 | 22.28 | 0.54 |

ND: Not Detected

As is apparent from Table 2, uroporphyrin I and uroporphyrin III were not detected in the normal mice and the mice to which the tumor-bearing cells had been intraperitoneally administered, before administration of δ-aminolevulinic acid hydrochloride, but uroporphyrin I and uroporphyrin III were detected in the normal mice and the mice to which the tumor-bearing cells had been intraperitoneally administered, after administration of δ-aminolevulinic acid hydrochloride, and both of uroporphyrin I and uroporphyrin III were detected in about 13 times higher amounts in the mice to which the tumor-bearing cells had been intraperitoneally administered, in comparison with the normal mice. In addition, while the ratio of uroporphyrin I to uroporphyrin III was 0.94 in the case of normal mice, the mice to which the tumor-bearing cells had been intraperitoneally administered showed a different value of 0.54. Based on this result, it was found that this is a diagnostic agent which can clearly distinguish the tumor tissue from the normal tissue based on the amounts of uroporphyrin I and uroporphyrin III and their ratio.

Example 4

A mouse tumor-bearing cell (MH 134 cell) was intraperitoneally administered to mice (C3H/He line, 5-week-old, female) at a dose of 1×10$^6$ cells, and they were reared for 0 to 14 days. Ten days after the intraperitoneal administration of tumor-bearing cells, 50 µl of 0.12 M δ-aminolevulinic acid hydrochloride was orally administered to the mice, and feces samples were collected 2 hours thereafter. To 10 mg in wet weight portion of the thus collected feces, 100 µl of an ethyl acetate-acetic acid mixture liquid (4/1, v/v) was added, the mixture was homogenized and then filtered using a filter paper, 10 µl of the filtrate was measured by HPLC (regarding the analyzing conditions, a fluorescence detector: excitation wavelength 406 nm, fluorescence wavelength 619 nm was used, a solution A: 80% acetonitrile/7% acetic acid/50 mM ammonium acetate mixture liquid and a solution B: 10% acetonitrile/4% acetic acid/50 mM ammonium acetate mixture liquid were used as the eluting solutions and subjected to a linear gradient of A/B (20/80)-A/B (90/10) for 30 minutes and then to the holding with solution A for 20 minutes, ODS-AGtypeCAPCELLPAK, 4.6 mmϕ×250 mm, particle diameter 5 µm (manufactured by Shiseido) was used as the column, and the measurement was carried out at a flow rate of 1.0 ml/min and at a temperature of 25° C.), and respective concentrations were calculated from the peak areas of standard solutions. In addition, 50 µl of 0.12 M δ-aminolevulinic acid hydrochloride was also administered to the normal mice as the control, and the same treatment was carried out. The results are shown in Table 3.

As is apparent from Table 3, uroporphyrin and coproporphyrin were not detected in the normal mice and the mice to which the tumor-bearing cells had been intraperitoneally administered, before administration of δ-aminolevulinic acid hydrochloride, and uroporphyrin and coproporphyrin were not detected also in the normal mice after administration of δ-aminolevulinic acid hydrochloride, but 1.75 pmol of uroporphyrin and 0.21 pmol of coproporphyrin were detected in the mice to which the tumor-bearing cells had been intraperitoneally administered, thus revealing that this is a diagnostic agent which can clearly distinguish the tumor tissue from the normal tissue.

Example 5

Those which were prepared by subcutaneously administering a human liver cancer cell (HepG2 cell) to nude mice (BALB/cA-nu, 5-week-old, male) at a dose of 1×10$^6$ cells, and those which were prepared by subcutaneously administering a human cervical cancer cell (HeLa cell) to nude mice (BALB/cA-nu, 5-week-old, female) at a dose of 1×10$^6$ cells, were reared for 0 to 10 days. To each of the respective mice of 10 days after the administration of human liver cancer cells or human cervical cancer cells, 50 µl of 0.12 M δ-aminolevulinic acid phosphate was orally administered, and urine was collected 4 hours thereafter.

The thus collected urine was measured by HPLC (regarding the analyzing conditions, a fluorescence detector: excitation wavelength 406 nm, fluorescence wavelength 619 nm was used, A: 80% acetonitrile/7% acetic acid/50 mM ammonium acetate and B: 10% acetonitrile/4% acetic acid/50 mM ammonium acetate were used as the eluting solutions and subjected to a linear gradient of A/B (20/80)-A/B (90/10) for 13 minutes and then to elution with solution A for 10 minutes, ODS-AGtypeCAPCELLPAK, 4.6 mm×250 mm, particle diameter 5 µm (manufactured by Shiseido) was used as the column, and the measurement was carried out at a flow rate of 1.0 ml/min and at a temperature of 25° C.), and each concentration was calculated from the standard solutions. Further, the urine concentration was corrected by measuring the amount of creatinine (CRE) in urine, and calculating the amount of porphyrin per CRE. In addition, 50 µl of 0.12 M δ-aminolevulinic acid phosphate was also administered to the normal nude mice as the control, and the same treatment was carried out. The results are shown in Table 4.

TABLE 3

Determination of uroporphyrin and coproporphyrin in feces by HPLC

| | Before administration (pmol) | | Before administration (pmol) | |
|---|---|---|---|---|
| | Uroporphyrin | Coproporphyrin | Uroporphyrin | Coproporphyrin |
| Normal mice | ND | ND | ND | ND |
| Tumor-bearing mice | ND | ND | 1.75 | 0.21 |

ND: Not Detected

TABLE 4

| Determination of uroporphyrin and coproporphyrin in urine by HPLC | | | | |
|---|---|---|---|---|
| | Before administration (μmol/g-CRE) | | After administration (μmol/g-CRE) | |
| | Uroporphyrin | Coproporphyrin | Uroporphyrin | Coproporphyrin |
| Normal mice | 0.06 | 0.06 | 0.16 | 0.99 |
| Tumor-bearing mice (human liver cancer cell) | 0.03 | 0.05 | 2.47 | 1.44 |
| Tumor-bearing mice (human cervical cancer cell) | 0.01 | 0.03 | 15.1 | 2.66 |

As is apparent from Table 4, it was found that after the administration of δ-aminolevulinic acid phosphate, about 15 times larger amount of uroporphyrin and about 1.5 times of coproporphyrin than those of the case of normal mice were contained in the urine of the mice to which human liver cancer cells had been administered. In addition, it was found that about 94 times larger amount of uroporphyrin and about 2.7 times of coproporphyrin than those of the case of normal mice were contained in the urine of the mice to which human cervical cancer cells had been administered.

Based on the above, it was found that the tumor diagnostic agent of the present invention is a diagnostic agent which can clearly distinguish normal from abnormal even when human tumor cells are used.

While the invention has been described in detail and with reference to specific embodiments thereof, it will be apparent to one skill in the art that various changes and modifications can be made therein without departing from the spirit and scope thereof.

This application is based on Japanese patent application No. 2004-284078 filed on Sep. 29, 2004 and Japanese patent application No. 2005-232996 filed on Aug. 11, 2005, the entire contents of which are incorporated hereinto by reference. All references cited herein are incorporated in their entirety.

INDUSTRIAL APPLICABILITY

According to the tumor diagnostic agent of the present invention, early stage detection, monitoring of therapeutic effect and prognostic diagnosis of tumors can be carried out conveniently without limitation to a specific tumor.

The invention claimed is:

1. A method for detecting the presence of tumors which comprises orally administering to a subject in need of said detecting δ-aminolevulinic acid represented by formula (I):

$$R^2R^1NCH_2COCH_2CH_2COR^3 \qquad (I)$$

wherein $R^1$ and $R^2$ each independently represents hydrogen and $R^3$ represents hydroxy or alkoxy or a salt thereof, collecting a sample from said subject and then measuring the concentration of porphyrins in the sample to thereby detect the presence of said tumors, wherein the sample is collected from the inside or outside of the body and is blood, body fluid, urine, feces, saliva, sweat, cerebrospinal fluid, semen or tears, wherein the porphryins are uroporphyrin, coproporphyrin, uroporphyrin I, uroporphyrin III, coproporphyrin I, or coproporphyrin III, and wherein the sample is collected from the inside or outside of the body after from 0.1 to 10 hours of the administration of the δ-aminolevulinic acid or salt thereof.

2. The method according to claim 1, wherein the tumor is in the brain, nasal tract, nasal cavity, trachea, bronchus, oral cavity, pharynx, esophagus, stomach, breast, colorectum, lung, ovary, central nervous system, liver, bladder, urethra, ureter, pancreas, cervical duct, abdominal cavity, anal canal or cervix uteri.

3. The method according to claim 1, wherein uroporphyrin I and uroporphyrin III are measured, and a tumor is detected based on the uroporphyrin/uroporphyrin III concentration ratio.

4. The method according to claim 1, wherein the porphyrins are measured using HPLC (high performance liquid chromatography), TLC (thin layer chromatography), fluorescence detection or immunoassay.

5. The method according to claim 1, wherein the porphyrins are measured using HPLC (high performance liquid chromatography) or TLC (thin layer chromatography).

* * * * *